United States Patent [19]

Porenski, Jr. et al.

[11] 4,414,841
[45] Nov. 15, 1983

[54] METHOD AND APPARATUS FOR DETERMINING PERCENT SOLIDS IN A SLURRY

[75] Inventors: Harry S. Porenski, Jr.; Earl E. Kohnhorst, both of Louisville, Ky.

[73] Assignee: Brown & Williamson Tobacco Corporation, Louisville, Ky.

[21] Appl. No.: 280,200

[22] Filed: Jul. 6, 1981

[51] Int. Cl.³ ............................................. G01N 15/06
[52] U.S. Cl. ................................................... 73/61 R
[58] Field of Search .................. 73/61 R, 53, 597, 599

[56] References Cited

U.S. PATENT DOCUMENTS

| | | | |
|---|---|---|---|
| 3,093,998 | 6/1963 | Albertson et al. | 73/61 R |
| 3,111,839 | 11/1963 | Evans et al. | 73/61 R |
| 3,269,172 | 8/1966 | McGaughey | 73/61 R |
| 3,320,428 | 5/1967 | Wagstaffe et al. | 73/53 X |
| 3,719,090 | 3/1973 | Hathaway | 73/61 R X |
| 3,729,987 | 5/1973 | Chao et al. | 73/61 R |

*Primary Examiner*—Gerald Goldberg
*Assistant Examiner*—Joseph W. Roskos
*Attorney, Agent, or Firm*—Charles G. Lamb

[57] ABSTRACT

A method for determining the percent of solids in a solid-liquid mixture or slurry by heating the slurry, removing vapor formed by heating the slurry, passing an ultrasonic signal through the heated slurry, and measuring the velocity and alteration of the ultrasonic signal in the slurry. An apparatus for carrying out this method includes a measuring loop in flow communication with a slurry processing system which includes a slurry heating device, a device for removing vapors from the heated slurry and an ultrasonic generating and measuring device.

6 Claims, 1 Drawing Figure

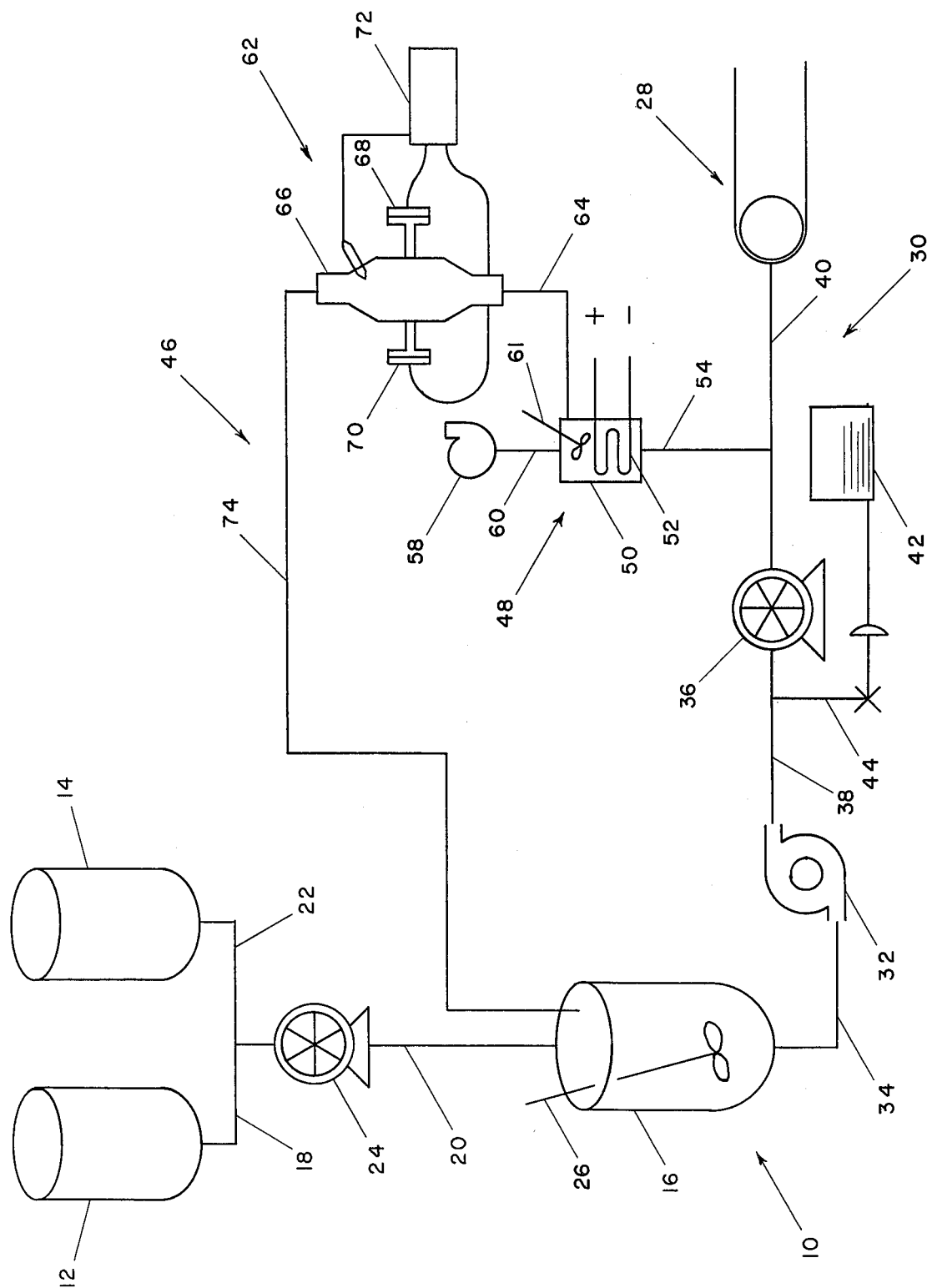

METHOD AND APPARATUS FOR DETERMINING PERCENT SOLIDS IN A SLURRY

BACKGROUND OF THE INVENTION

The present invention relates to determining the solids content in a solid-liquid mixture, and more particularly to determining the percent of solids content in a solids-liquid mixture by measuring the speed of sound in the solids-liquid mixture.

Many various industrial processes use a solids-liquid mixture either as an interim step or as an end product. It is important for a consistent end product that the percent of solids in the slurry be accurately controlled. Of course, the solids content must be accurately determined before it can be controlled.

One heretofore known method of determining the solids content in a slurry is to extract a sample of the slurry from a production process. The sample is weighed, then dried to eliminate the liquid, and the resulting residue of solids weighed. The weight of the residue of solids is compared to the weight of the slurry sample which gives the percent of solids in the slurry sample. This method takes a substantial period of time. Theoretically, from a quality control standpoint, during the time it takes to determine the solids content in the slurry sample, the production process should be suspended. Production downtime, however, is non-productive and adds to the cost of the end product. Realistically, the production process is usually continued while the testing process is being done even though the solids content in the production slurry may be deviant from the desired level. Another drawback with this testing method is that the slurry sample is not necessarily truly representative of the entire slurry. Yet a further drawback is that, because the production process is continuing during the time it takes to determine the solids content in the slurry sample, by the time the solids content of the sample is determined the percent of solids in the production slurry may have changed from the time the slurry sample was taken. In other words, the solids determining process does not render a "real time" measurement of the solids content in the slurry.

It is known that the solids content in a solid-liquid mixture can be determined by measuring the speed of sound through the mixture. However, these heretofore known ultrasonic measuring systems and methods are limited by the temperature of the mixture and percent of solids in the mixture. These systems and methods seem to be limited to measuring the solids content in a solids-water slurry having a maximum temperature of from about 130° F. to 140° F., and to accurately measure the solids content in a slurry having from about 1% to 6% solids.

SUMMARY OF THE INVENTION

The present invention recognizes the drawbacks of the heretofore known systems and methods for determining the solids content in a solid-liquid mixture or slurry, and provides a solution to these drawbacks and limitations.

The present invention provides a system and method for determining the solids content of a slurry on a "real time" basis and is therefore advantageously useful for determining the solids content of a slurry in a production process. Furthermore, the present invention provides a system and method for determining the solids content of a slurry at higher slurry temperatures and higher solids concentration than the heretofore known systems and methods.

More particularly, the present invention provides a method for determining the percent of solids in a solids-liquid mixture comprising the steps of continuously drawing off a sample of the solids-liquid mixture, heating the sample to a temperature high enough to form vapor without boiling the liquid component of the sample, removing the vapor generated by heating the liquid component of the sample, passing the sample through an ultrasonic signal generating and measuring device, passing an ultrasonic signal through the heated sample, measuring the velocity and attenuation of the ultrasonic signal in the heated sample, and continuously returning the sample back to the solids-liquid mixture from which it was drawn.

The present invention further provides a system for determining the percent of solids in a solids-liquid mixture comprising means for heating a sample of the solids-liquid mixture to a temperature sufficiently high enough to form vapor without boiling the liquid component of the sample, means establishing continuous flow communication between the solids-liquid mixture and the heating means for continuously drawing samples from the solids-liquid mixture to the heating means, means for applying a vacuum to the heated sample for removing vapor generated by heating the sample, an ultrasonic signal generating and signal measuring device, means establishing continuous flow communication between said heating means and said ultrasonic signal generating and signal measuring device for continuously moving the heated sample from the heating means to the ultrasonic signal generating and measuring device, and means establishing continuous flow communication from the ultrasonic signal generating and measuring device back to the solids-liquid mixture for continuously returning the sample back to the solids-liquid mixture from which it was drawn.

DESCRIPTION OF THE DRAWING

A better understanding of the present invention can be had upon reference to the following specification and accompanying FIGURE which illustrates, in diagrammatic form, a system for determining the percent of solids in a solids-liquid mixture embodying various features of the present invention.

DETAILED DESCRIPTION

The FIGURE diagrammatically illustrates a manufacturing process utilizing a solids-liquid mixture or slurry.

The illustrated system, generally denoted as the numeral 10, for carrying out the manufacturing process consists of a tank 12 containing a primary slurry of from, for example 2 to 3 percent solids, and a storage tank 14 containing dry solids. The primary slurry tank 12 and solids storage tank 14 are in flow communication with a mixing tank 16 wherein the primary slurry and solids are mixed to form a resulting slurry. The primary slurry flows from the primary slurry tank 12 through a branch conduit 18 to a mixing tank supply conduit 20, and the solids flow from the solids storage tank 14 through a branch conduit 22 to the mixing tank supply conduit 20. Both the primary slurry and solids flow to the mixing tank 16 in the supply conduit 20. A blender 24 can be located in the mixing tank supply conduit 20 to pre-mix the primary slurry and solids and to reduce the size of the solids before discharge into the mixing tank 16.

The mixing tank 16 includes an agitator 26 to thoroughly mix the primary slurry and solids to obtain a homogeneous resulting slurry. The resulting slurry is conveyed from the mixing tank 16 to a work station 28 through a transfer system, generally denoted by the numeral 30. As shown, the transfer system comprises a slurry moving pump 32 having its inlet side in flow communication with an outlet from the mixing tank 16 through a conduit 34, a blender 36 for further homogenizing the slurry in flow communication with the outlet side of the pump 32 through a conduit 38, and a slurry supply conduit 40 in flow communication with the blender 36 for delivering the slurry to the work station 28.

A water tank 42 is in flow communication with the slurry in the transfer system 30 by means of a conduit 44 interconnected to the conduit 38. Water can be selectively added to the slurry flowing in the transfer system 30 to adjust the liquid content of the slurry.

A system generally denoted by the numeral 46, for determining the solids content of the slurry is in flow communication with the slurry flowing in the transfer system 30 and the slurry mixing tank 16 thus forming a closed loop system. The system 46 for determining the percent of solids in the slurry (solids-liquid mixture) comprises heating means, generally denoted by the numeral 48, for heating a sample of the slurry to a temperature sufficiently high to form and drive-off entrapped vapor without boiling the liquid component of the sample. The heating means 48, as shown, consists of a sample container 50 having a heat generating device 52 such as, for example, a resistance heating coil. Other heat generating devices, however, can be used as may be convenient, such as steam. The sample heating means 48 is in continuous flow communication with the slurry through a conduit 54 connecting the slurry supply conduit 40 of the transfer system 30 to the sample container 50. Vacuum means, generally denoted by the numeral 58, provides a vacuum condition to the heated sample in the slurry container 50. The vacuum means 58 can be a blower or pump having its low pressure side in communication with the interior of the slurry container 50 through a conduit 60 subjecting the heated sample to a vacuum for removing the vapor coming out of the heated sample. An agitator device 61 can be included in the sample container 50 to maintain the homogenization of the sample and to aid in moving entrapped vapor bubbles to the surface of the sample. An ultrasonic signal generating and signal measuring device 62 is included in the closed loop system 46. As shown, the ultrasonic signal generating and measuring device 62 is in flow communication with the sample container 50 of the heating means 48 through a conduit 64. The ultrasonic signal generating and measuring device 62 can be of the type having a flow-through housing 66 defining a path for the passage therethrough of the heated sample from the heating means 48. The ultrasonic device 62 includes at least one pair of transducers 68 and 70 located opposite each other on either side of the sample path through the housing 66 and a control unit 72 for generating an electrical signal. The flow-through housing 66 of the ultrasonic signal generating and measuring device 62 is also in flow communication with the mixing tank 16 through a conduit 74 so that the sample is returned to its source.

In the illustrated process, the slurry is formed by mixing the primary slurry, having for example from about 2 to 3 percent solids from the primary slurry tank 12 with solids from the solids tank 14 by channeling these components through branch conduits 18 and 22, respectively, to the mixing tank supply conduit 20 and subsequently into the mixing tank 16. As these components flow together through the mixing tank supply conduit 20, they move through the blender 24 which preliminarily mixes the components and reduces the size of the solids component to a maximum of, for example, 50 microns. The primary slurry and solids are thoroughly mixed in the mixing tank 16 by the agitator 26 to obtain a homogeneous solids-liquid mixture of higher solids content than the primary slurry, for example, from about 10 to 12 percent solids. The homogenized resulting slurry is moved from the mixing tank 16 through the transfer system 30 by the pump 32. As the resulting slurry moves through the transfer system 30 to the work station 28 it passes through the blender 36 to assure continued homogenization of the resulting slurry.

As the resulting slurry moves toward the work station 28, a sample is continuously drawn off into the solids content determining loop 46. As illustrated, the sample flows through the conduit 54 from the slurry supply conduit 40 into the sample container 50 of the heating means 48. In the heating means 48, the sample is heated by the heat generating device 52 to a temperature sufficient to initiate the formation of vapor without boiling the liquid component of the slurry sample to drive off entrapped gas in the sample. As the slurry sample is heated, it is also agitated by the agitating means 61 to maintain the homogeneousness of the sample and to promote the migration of entrapped vapor bubbles to the surface of the slurry sample. The vapors coming off the liquid component of the slurry sample are removed from the sample container 50 of the heating means 48 by, for example, subjecting the slurry sample to a vacuum condition created by the vacuum pump 58. The heated slurry sample is continuously passed to the ultrasonic signal generating and measuring device 62 from the sample container 50 through the conduit 64. As the heated slurry sample passes through the flow-through housing 66 of the signal generating and measuring device 62 the control unit 72 generates an electric signal which is converted to an ultrasonic signal by one of the transducers 68. The signal is directed across the path of the sample surry moving through the housing 66 and is received at the other tranducer 70 which reconverts the ultrasonic signal to an electrical signal. The reconverted electrical signal is amplified by the control unit which also measures the sonic velocity and attenuation of the signal through the slurry sample. This information is then compared to known data correlating sonic velocity and signal attenuation to various percent solids in the slurry. Thus, the percent solids in the slurry sample is readily determined. After passing through the ultrasonic signal generating and measuring device 62, the slurry sample is returned to its source in, for example, the mixing tank 16 and mixes back with the resulting slurry.

The above-described process is continuously conducted as long as a resulting slurry is being formed and moving through the transfer system 30. Thus, the process yields "real time" results of the percent solids in the resulting slurry. This allows the solids content in the resulting slurry to be controlled as it is being formed without delay and results in a uniform product.

The solids content in the resulting slurry can be affected in a number of ways. If the solids content is too high, additional liquid can be added. This can be accomplished by adding liquid to the mixing tank 16 or, as illustrated, by introducing additional liquid into the transfer system 30 from the water tank 42 through the conduit 44. If the solids content is too low, additional solids can be added to the resulting slurry from the solids storage tank 14.

It has been found that the above described method and apparatus will accurately determine the solids content in a slurry having a higher solids content than the heretofore known methods and apparatus. Accurate results have been obtained with slurries having from about 10 to 11 weight percent solids content.

In a production environment, the method and apparatus of the present invention result in a more uniform production or resulting slurry because of the "real time" measurements of the actual resulting or production slurry which allows corrections to be made immediately to the slurry. Furthermore, because the present invention can determine higher solids content than the heretofore known methods and apparatus, the reuslting slurry can be of a higher solids concentration. This results in money savings in a production process because a smaller volume of slurry can be moved to the work station to deliver the same amount of useful solids to the work station.

The foregoing detailed description is given primarily for clarity of understanding and no unnecessary limitations should be understood therefrom for modifications will be obvious to one skilled in the art upon reading this disclosure and may be made without departing from the spirit of the invention or the scope of the appended claims.

What is claimed is:

1. A method for determining the percent of solids in a solids-liquid mixture, the solids being at least two percent by weight of the mixture, comprising the steps of:
   continuously drawing off a sample of the solids-liquid mixture;
   heating said sample to a temperature sufficiently high enough to form vapor without boiling the liquid component of said sample;
   removing the vapor generated by heating the liquid component of said sample;
   continuously passing said heated sample through an ultrasonic signal generating device;
   continuously passing an ultrasonic signal through said heated sample;
   continuously measuring the velocity and attenuation of the ultrasonic signal in said heated sample;
   determining the percent of solids in the solids-liquid mixture corresponding to the measured sonic velocity and attenuation of the ultrasonic signal; and,
   continuously returning said sample back to the solids-liquid mixture from which it was drawn.

2. The method of claim 1, wherein the vapor generated by heating said sample is drawn off by subjecting said heated sample to a vacuum condition.

3. The method of claim 1, further comprising the step of agitating said heated sample to release vapor bubbles entrapped in said heated sample.

4. A system for determining the percent of solids in a solids-liquid mixture, the solids being at least two percent by weight of the mixture, comprising:
   means for continuously heating a sample of the solids-liquid mixture to a sufficiently high temperature to form vapor without boiling the liquid component of said sample;
   means establishing continuous flow communication from the solids-liquid mixture to said heating means for continuously drawing said sample from the solids-liquid mixture to said heating means;
   an ultrasonic signal generating and signal measuring device for continuously directing an ultrasonic signal through said sample and measuring the velocity and attenuation of the signal in said sample thereby providing for the continuous determination of the percent of solids in said sample;
   means establishing continuous flow communication from said heating means to said ultrasonic signal generating and signal measuring device for continuously moving said heated sample from said heating means to said ultrasonic signal generating and measuring device; and,
   means establishing continuous flow communication from said ultrasonic signal generating and measuring device back to said solids-liquid mixture for continuously returning said sample back to the solids-liquid mixture from which it was drawn.

5. The system of claim 4, further comprising means for agitating said heated sample to release vapor bubbles entrapped in said heated sample.

6. The system of claim 4, wherein said means for continuously removing vapor from heating means comprises means for applying a vacuum condition to said heated sample.

* * * * *